United States Patent [19]

Williams

[11] Patent Number: 4,572,172
[45] Date of Patent: Feb. 25, 1986

[54] MOLDING CAST SYSTEM FOR FRACTURES OF THE HUMERUS AND OF THE RADIUS ULNA

[76] Inventor: L. Benton Williams, P.O. Box 916, Georgetown, S.C. 29440

[21] Appl. No.: 552,414

[22] Filed: Nov. 16, 1983

[51] Int. Cl.⁴ ............................................. A61F 5/40
[52] U.S. Cl. ................................................... 128/94
[58] Field of Search ............... 128/91 R, 94, 90, 87 R, 128/89 R

[56] References Cited

U.S. PATENT DOCUMENTS

| 3,706,310 | 12/1972 | Garnett | 128/94 |
| 4,143,655 | 3/1979 | Custer et al. | 128/90 |
| 4,193,395 | 3/1980 | Gruber | 128/90 |
| 4,232,664 | 11/1980 | Blatt | 128/94 |

Primary Examiner—John D. Yasko
Assistant Examiner—Christa K. Scott
Attorney, Agent, or Firm—Quaintance, Murphy & Presta

[57] ABSTRACT

A molding cast system for fractures of the humerus and of the radius and ulna that includes a molding cast having a wall member forming a substantially horizontal chamber for holding the forearm and a substantially vertical chamber for holding the upper arm, with an elongated aperture along the top of the horizontal chamber and an elongated aperture along the front of the vertical chamber. Connectors having fasteners hold the edges of the wall member defining the apertures together. A neck sling is affixed to the wall member. The wall member has an outer layer of soft flannel; a middle layer of a laminated plaster of paris casting material; and an inner layer of a flexible porous material next to the skin. The molding cast is prefabricated and can be shipped in a rolled condition to a hospital or doctor's office where it can be treated to be made pliable for specific application to a patient.

10 Claims, 5 Drawing Figures

MOLDING CAST SYSTEM FOR FRACTURES OF THE HUMERUS AND OF THE RADIUS ULNA

BACKGROUND OF THE INVENTION

This invention relates generally to casts for fractures of the arm and in particular to new and improved molding casts for fractures of the humerus and fractures of the radius and ulna.

When a physician encounters a fractured humerus that after alignment of the bone must be externally secured by a cast, he prepares a molding cast that encloses the arm so as to immobilize the fracture site. The preparation of the molded cast takes place at the hospital or physician's own treatment area and is generally done specially for each patient. Specifically, plaster of paris strips are formed in rolls by the manufacturer and shipped to the hospital or physician. The plaster of paris strips are in fact individual strips of cloth mesh that has been impregnated with, and to some degree overlaid by, the plaster of paris and rolled while wet prior to shipment. The plaster of paris rolls are stored dry at the hospital. When a physician needs to prepare a cast, he measures the patient's arm for the length of plaster of paris strip he needs, then wets the foll, unrolls it, cuts the strip according to his requirement, and applies or molds it to the patient's arm. This process in general is repeated for four, five, or six layers or strips of the plaster of paris. The application is done so as to completely enclose the arm of the patient. Drying on the outside of the molded cast occurs in about two hours, but complete drying takes considerably longer.

A few observations can be made about the above procedure. One is that the procedure set forth takes considerable time, since it is a step-by-step wetting, cutting and molding process repeated for a number of layers. Another comment that can be made is that the arm of the patient has been completely enclosed, partly of necessity, for that is the only way the cast will remain in the proper position on the patient. The result of this complete enclosure is the possible occurrence of a circulation problem in the patient's arm. Finally, it may be noted that the drying process, because of the complete enclosure of the layered strips, takes a considerable time to complete.

The present invention attempts to overcome the limitations of prior art devices by providing an intermediate cast that can be activated by heating or immersing in water at the hospital. The cast does not completely surround the body member so as to provide adequate circulation.

Prior patents that disclose various types of casts or splints that are activated by heat so as to soften the casting material are as follows:

| Inventor | U.S. Pat. No. |
| --- | --- |
| Larson | 3,853,124 |
| Arluck | 4,006,741 |
| Arluck | 4,136,686 |
| Custer et al | 4,143,655 |
| Gruber | 4,193,395 |

The Arluck patents also describe devices that do not completely surround the body member.

The following patents describe moisture-activated casting material in a laminated structure or two mutually reactive substances that are separated in the splint and thereafter intermixed to harden the splint when it is in the proper position.

| Inventor | U.S. Pat. No. |
| --- | --- |
| Parker | 2,960,984 |
| Blomer et al | 4,060,075 |

The following patents are pertinent in that they disclose surgical slings of various types having neck straps and buckles for adjusting the positions of the straps:

| Inventor | U.S. Pat. No. |
| --- | --- |
| Messer | 2,875,754 |
| Johnson | 3,554,194 |
| Garnett | 3,706,310 |
| Blatt | 4,232,664 |

The following patents are of some interest as they disclose temporary splints or the like that only partially surround a body member and may have straps or the like for holding them in place:

| Inventor | U.S. Pat. No. |
| --- | --- |
| Finnieston | Des. 255,384 |
| Finnieston | Des. 255,602 |
| Finnieston | Des. 255,603 |
| Schloss | 3,800,789 |

Although prior art molded cast procedures have performed well, nevertheless, more economical, efficient and safer casting operations are desirable. Saving of the physician's time, greater patient comfort, and reduction of circulation problems for the patient are possible with a prefabricated cast having an open top portion.

SUMMARY OF THE INVENTION

Accordingly, it is an object of the present invention to provide a molding cast for a fracture of the humerus that can be prefabricated by a manufacturer and applied to a patient by a physician in a simple, rapid and efficient manner.

It is yet another object of the present invention to provide a prefabricated molding cast for a patient's fractured humerus that has an open top portion that encourages normal circulation of blood in the area of the cast.

It is yet another object of the present invention to provide a prefabricated molding cast for a fractured humerus that can be preselected according to size of the patient's arm and easily, quickly and efficiently placed upon the patient's arm.

It is yet another object of the present invention to provide a prefabricated molding cast for a fractured humerus and simple fractures of the radius and/or ulna.

The molding cast for fractures of the humerus and simple fractures of the radius and ulna in accordance with the present invention includes a molding cast system for fractures of the humerus and of the radius and/or ulna of a patient that comprises a molding cast that includes a wall member forming connecting, approximately cylindrical, first and second chambers, the first chamber receiving the forearm of the patient and the second chamber receiving the lower part of the upper arm. An elongated aperture is formed between opposed elongated side edges of the wall member and extends substantially horizontally and faces upwardly between the hand area and the elbow area, and further extends substantially vertically and faces forwardly between the elbow area and the lower part of the upper arm area. Preferably, four connectors, having releasable connecting portions are affixed to the side edge portions of the wall member, the four connectors being adjustable and being adapted to removably connect the side edge portion across the aperture. A neck sling is provided that includes a strap member that is affixed to the wall member.

The wall member comprises an inner layer of a porous, flexible, soft, water absorbing material such as sponge rubber on a foam plastic that is positioned next to the skin of the patient; a middle layer of a plurality of laminated layers of a plaster of paris casting material; and an outer layer of a flexible, soft, water absorbing, fast drying material, such as flannel or the like. The number of middle laminated layers preferably includes approximately twenty (20) layers.

The present invention is also directed to a method of making and applying a molding cast. The method includes preparing the wall member at the manufacturer, affixing the connectors and sling, rolling up the molding cast after it has been cut to size according to one of a number of sizeing patterns, and shipping the cast to, for example, a hospital or a physician. At the hospital, the cast is stored until needed. At that time, the cast is treated, preferably by placing it in water or by subjecting it to heat, to make it pliably soft. It is then unrolled and molded around the patient's arm. An "Ace" bandage may be wrapped around the soft cast, the sling is adjusted around the neck of the patient, and the connectors affixed. When the cast is dry and rigid, the "Ace" bandage is removed.

The present invention will be better understood and the main objects and important features other than those set forth above will become apparent when consideration is given to the following details and description, which when taken in conjunction with the annexed drawings, describes, discloses illustrates and shows the preferred embodiments or modifications of the present invention and what is presently considered and believed to be the best mode of practice in the principles thereof. Other embodiments or modifications may be suggested to those having the benefit of the teachings herein, and such other embodiments or modifications are intended to be reserved especially as they fall within the scope and spirit of the subjoined claims.

DESCRIPTION OF THE PREFERRED EMBODIMENTS

Figure 1:
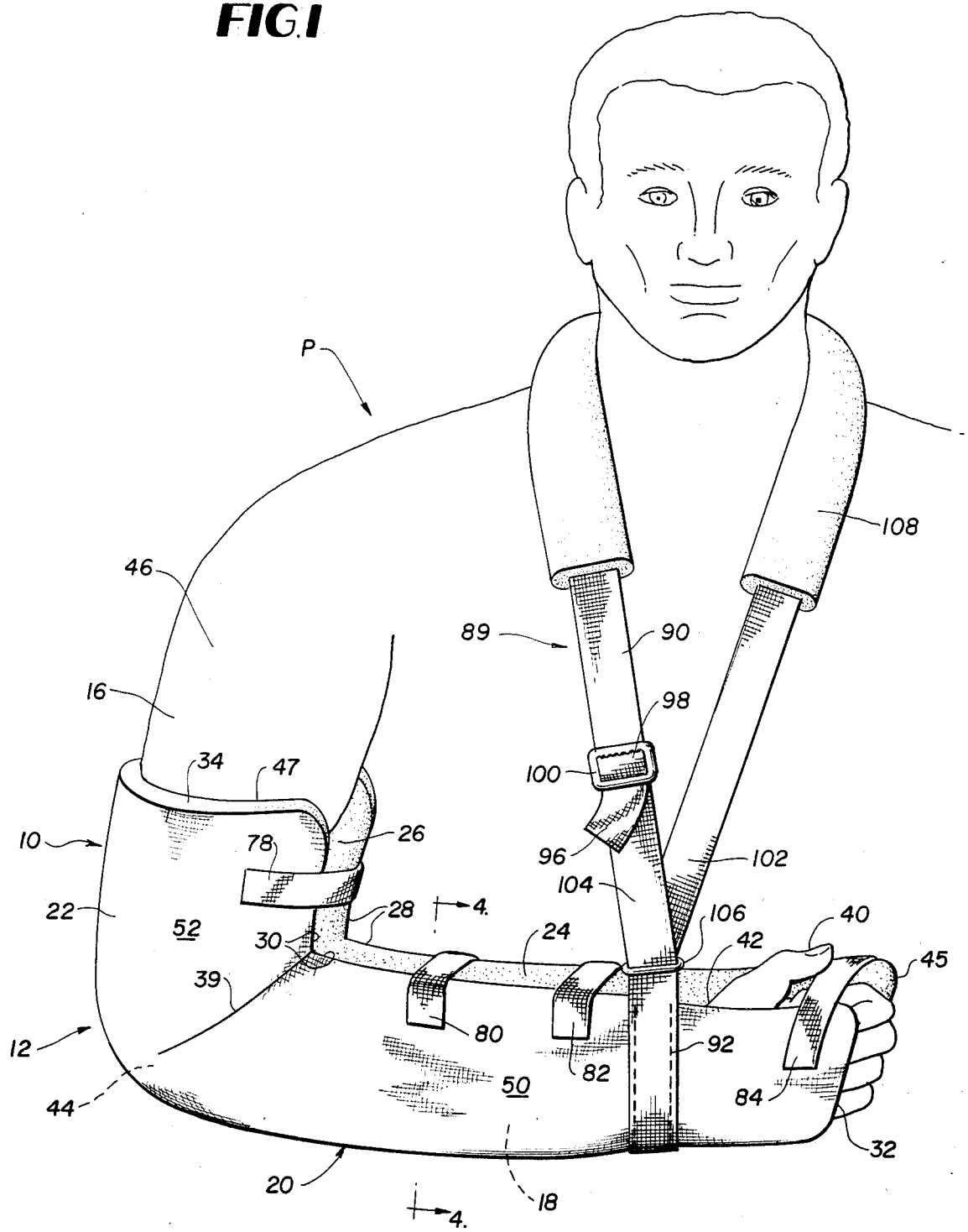
FIG. 1 is a perspective view showing the molding cast of the present invention in position on the right arm of a patient.

Reference is now made to the drawings and in particular to FIGS. 1-5 in which identical or similar parts are designated by the same reference numerals throughout.

A molding cast system 10 is illustrated in perspective in FIG. 1 attached to a fractured arm 12 of a patient P. The molding cast system 10 can be used to treat either a fracture of the humerus of the upper arm 16 or a simple fracture of the radius or the ulna of the forearm 18, or fractures of both the humerus and a simple fracture of the radius and/or ulna. The type of fracture or fractures being treated in the description herein of molding cast system 10 will not be further treated herein.

Molding cast system 10 includes a molding cast 20 that includes a substantially elongated wall member 22 that forms connecting, approximately cylindrical first and second chambers 24 and 26, respectively. Wall member 22 has a pair of opposed, spaced elongated inner and outer side edge portions 28 and 30 and a pair of end edge portions 32 and 34 that intersect side edge portions 28 and 30 in positions to be described.

First chamber 24 extends generally horizontal as seen in FIG. 1 for reasons of inmobility and an optimum healing position. The actual position of first chamber 24 may vary somewhat from the horizontal, depending on the fracture to be treated. First chamber 24 is adapted to receive the under and side portions of the forearm 18. It is noted that the terms "under part" and "side parts" are used herein in a special manner that descriptively indicates the position of the forearm 18 relative to first chamber 24 as forearm 18 is positioned in fact in the molding cast 20.

In FIG. 1, it can be seen that the thumb 40 is positioned pointing generally vertically upwardly, so that the side of the wrist also is upward, and will be referred to herein as the "top part" of forearm 18 as will the continuation of the wrist continuing from the side of the wrist. First chamber 24 extends generally between the hand area 42 and the elbow area 44, with end edge portion 32 being positioned across hand 42 below the thumb 40.

Second chamber 26 is generally vertical and encloses the rear and side parts of upper arm 16. Again, the terms "rear part" and "side part" as used especially herein refer to those parts of upper arm 16 relative to second chamber 26 as upper arm 16 is in fact positioned in molding cast 20. Second chamber 26 extends from elbow area 44 to the shoulder area 46. As shown in FIG. 1, end edge portion 34 is spaced a short distance upwardly from elbow 44. This distance can vary depending on particular fracture conditions. End edge portion 34 defines an approximately circular first opening 45 at the hand end of first chamber 24; end edge portion 32 defines an approximately circular second opening 47 at the upper end of second chamber 26. Upper arm 16 extends through the second opening 47 into the second chamber 26, and hand 42 extends through first opening 45 into first chamber 24.

Elongated side edge portions 28 and 30, which as stated oppose one another, form between them an elongated aperture 48 that opens to first and second chambers 24 and 26 and that is disposed along the top part of forearm 18 and the forward part of upper arm 16. The terms "top part" and "forward part" are used herein in a similar manner as described earlier with reference to "bottom part", "side parts", and "rear parts" with the proviso that "front" and "rear" are terms relative to the torso of the patient P. As shown in FIG. 1, molding cast 20 has a first generally horizontal portion 30 that extends between hand area 42 and elbow area 44 and also has a continuing generally vertical portion 52 that extends generally upwardly towards the shoulder area 46 to a position spaced from elbow 44.

Figure 2:
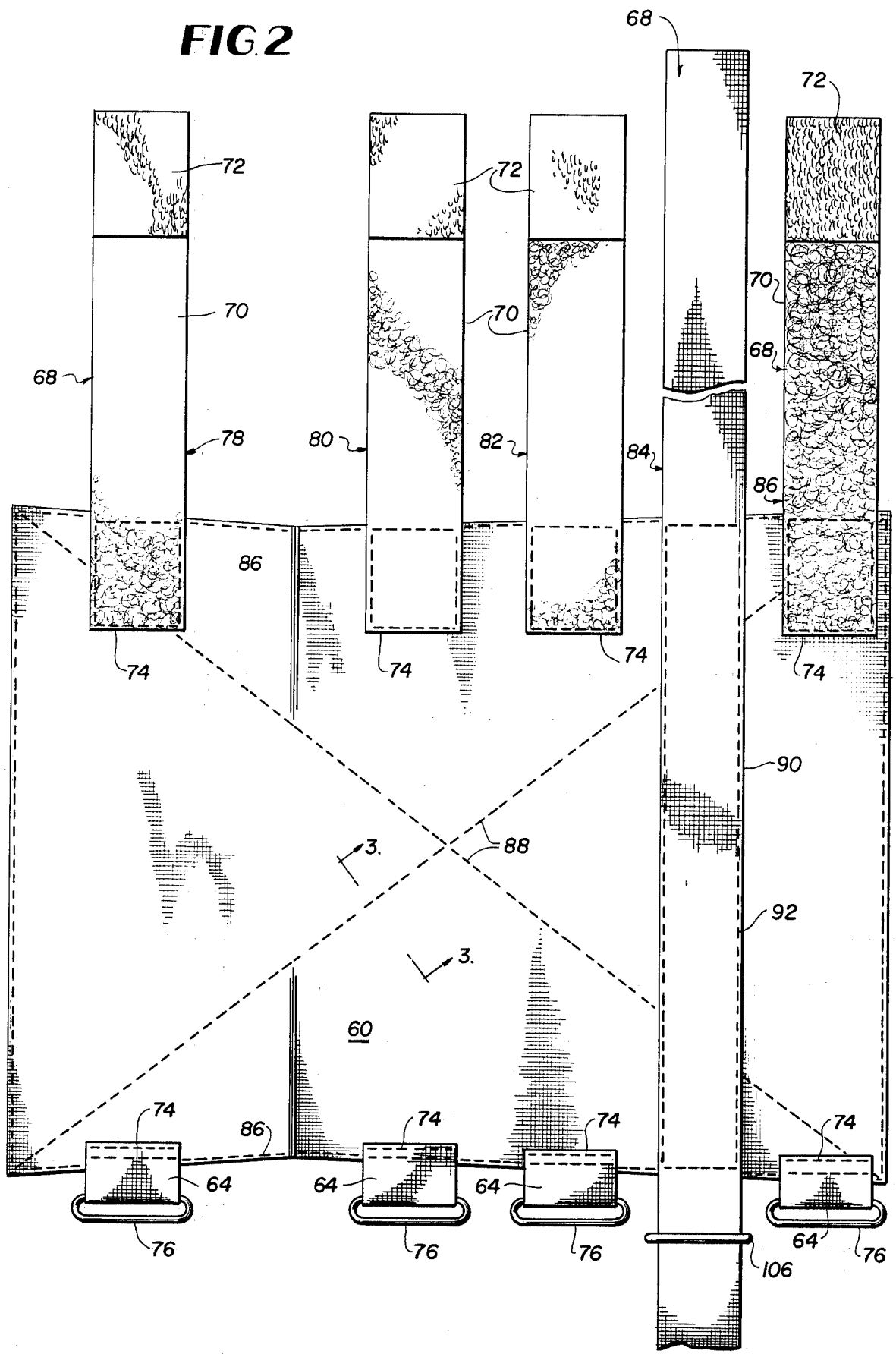
FIG. 2 is a top view of the molding cast in an open, or unrolled, mode prior to application to the arm of the patient with the outer layer of the cast shown.

The elongated aperture 48 extends from the first circular opening 45 at end edge portion 32 and extends generally horizontally along the top of molding cast 20 to elbow area 44; and then extends upwardly along the front of molding cast 20 from elbow area 44 to the end edge portion 34 above elbow area 44 to the second circular opening 47 at end edge portion 34. As can be seen in FIGS. 1 and 2, a crease or fold line 39 is formed in wall member 22 between horizontal and vertical portions 41 and 43, respectively, of molding cast 20.

Figure 4:
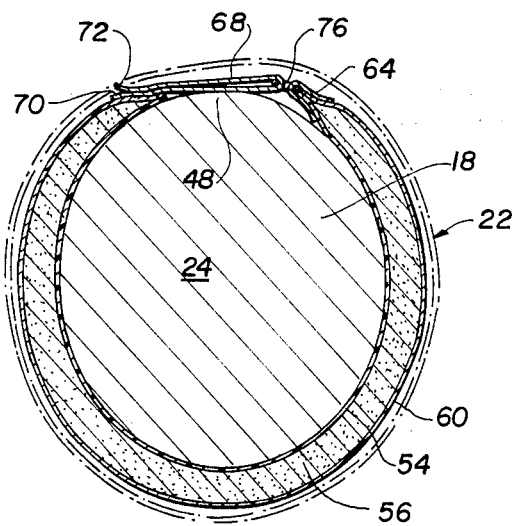
FIG. 4 is a sectional view taken substantially along line 4—4 of FIG. 1.

Attention is now directed to FIG. 2, which illustrates molding cast 20 in a flat, or open, position and to FIG. 4, which shows molding cast 20 in its assembled position as it is shown in FIG. 1. It is to be appreciated that molding cast 20 is first of all made at the manufacturer in a manner to be described, shipped to a hospital or doctor's office, and then molded on the patient's arm 16. Before proceeding with the finally assembled position shown in FIG. 1, a description of the construction of wall member 22 will first be set forth.

As seen in FIG. 4, wall member 22 includes an inner layer 54 of a porous, flexible, soft, water absorbing, fast drying material such as foam rubber or a foam plastic that is adapted to contact the skin of upper arm 16 and forearm 18 of patient P. Wall member 22 also includes, next to inner layer 54, a middle layer 56 formed of a plurality of laminated layers of a plaster of paris casting material known in the art. Each laminated layer 58 of plaster of paris casting material, best seen in FIG. 3, includes a strip of cloth mesh imp-egnated with, and to some degree overlaid by, standard plaster of paris. The exact number of laminated layers 58 of middle layer 54 may vary, but is approximately twenty (20) layers 58. Finally, wall member 22 includes next to inner middle layer 54 an outer layer 60 of a flexible, soft, water absorbing, fast drying material such as soft flannel.

Wall member 22 is shown in FIG. 4 in a curled position with outer layer 60 covering inner and middle layers 54 and 56.

Molding of the cast is accomplished by making wall member 22 pliable by the application of water or heat. The doctor then can mold wall member 22 to the patient's arm to the configuration shown in FIGS. 1 and 3.

As shown in FIGS. 1–4, molding cast system 10 also includes a plurality of releasable connectors, particularly shown as connectors 78, 80, 82, and 84, which will be further discussed below relating to positioning. Connector 80 will be discussed here as typical of the other connectors. As an illustrative example, connector 80 comprises a strap portion 64 secured to outer side edge portion 30 of the wall member; a connector strap portion 68 secured to the inner side edge portion 28 of the wall member and having releasable fastening means, such as Velcro or snag-and-hook fasteners 70, 72 secured to the outer end thereof; and a ring member 76 connected to the outer end of the strap portion 64. In operation, the connector strap portion 68 is extended across the elongated aperture 48 from the outer side edge portion 30, through the ring member 76, and then is bent back over itself to bring the fasteners 70, 74 into releasable engagement, as shown in FIG. 4. It will be readily seen that the connector strap 68 can be adjusted according to the particular requirements so as to keep inner and outer edge portions 28 and 30 firmly in position and, as a result, molding cast 20 in turn is kept firmly in position around the arm of the patient with a desired fit.

Preferably, the connecting means includes an upper arm connector 78 positioned between elbow area 44 and end edge portion 22, which keeps inner and outer edge portions 28 and 30 of second chambers 26 in position; and two spaced forearm connectors 80 and 82, which are positioned between elbow area 44 and the thumb 40, and one hand connector 84 positioned between thumb 40 and end edge portion 34, the latter three connectors determining the shape and size of the wall member and the first chamber 24. Within the scope of the present invention, the number and position of the connectors can be varied to suit particular needs.

Figure 3:
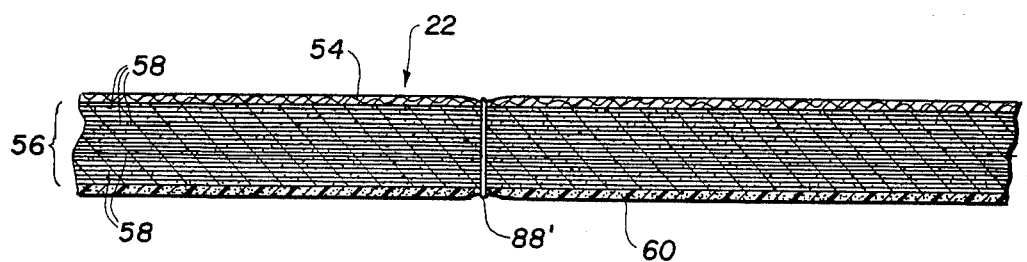
FIG. 3 is a sectional view taken substantially along line 3—3 of FIG. 2.

As shown in FIG. 2, the three layers 54, 56 and 60 are secured together along their edges by edge stitches 86 and cross stitches 88, which diagonally connect each opposing corner of the wall member 22. A typical through cross-stitch 88' is shown in FIG. 3 extending between inner and outer layers 54 and 60. Inner and outer strap portions 64 and 68 are likewise stitched at 74 along their inner ends to wall member 22.

Figure 5:
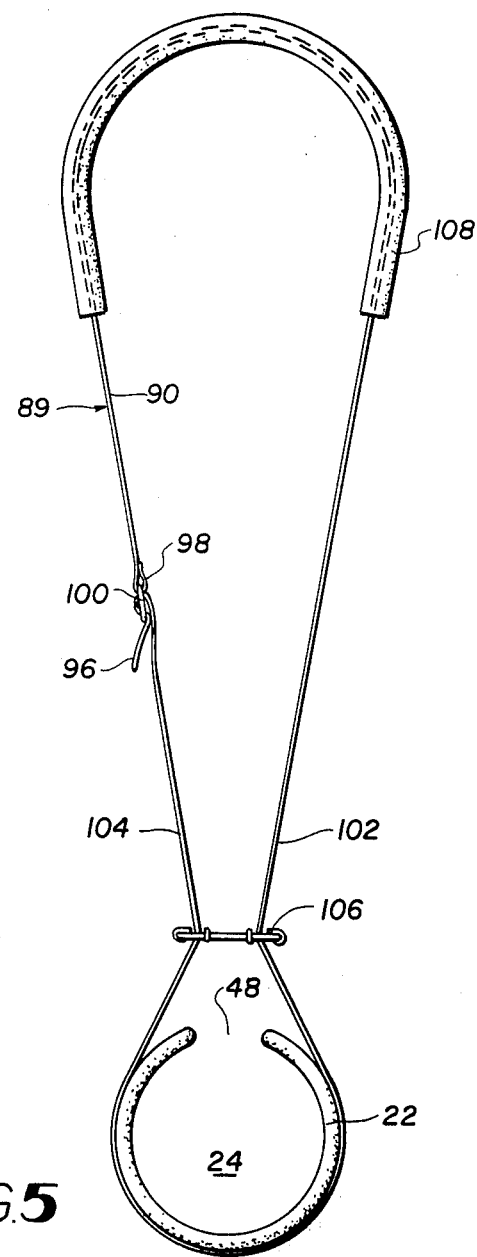
FIG. 5 is an end elevational view of the sling portion of the molding cast.

FIGS. 1, 2 and 5 particularly illustrate a sling 89 including a strap member 90 that is attached, preferably by stitching 92, to the underside of wall member 22, as shown in FIG. 2. Strap member 90 has a pair of ends 96 and 98 with a toothed buckle 100 or the like being connected to end 98. Strap member 90 extends from opposite undersides of wall member 22, one portion 102 extending from the rear of wall member 22 to the neck of patient P, and downwardly across the chest of the patient to the end 98 of buckle 100. The other portion 104 extends upwardly from the front of wall member 22 to end 96, which is adjustably and removably connected to buckle 100 at end 98 so as to position and maintain forearm 18 in first chamber 24 in a predetermined, generally horizontal position, and to position and maintain the upper arm portion 16 in second chamber 26 in a predetermined generally vertical position. Strap member 90 preferably includes a pinching ring 106 that is positioned directly over molding cast 20 and through which both strap portions 102 and 104 extend, as shown in FIG. 5. A purpose of the pinching ring 106 is to help align the fractured humerus and to maintain it in normal position. A soft padded neck protector 108 is provided and has an internal channel for receiving the portion 102 of strap member 90 therethrough, as also shown in FIG. 5.

It is to be appreciated that molding cast 20 is first formed at a manufacturer; prepared for shipment, preferably by rolling; and, upon receipt at the physician's office or hospital, molding cast 20 is then stored until needed. When needed, the cast is treated to make it soft and pliable, preferably either by placing it in water, or, alternatively, by heating it. The molding cast is then fitted to the patient's arm in a desired manner. An "Ace" bandage may then be placed over the cast until it is set in the desired shape. The "Ace" bandage is then removed. Molding cast 20 may be prepared in various sized patterns, such as small, medium, and large so as to give the doctor flexibility in selection according to the size of the patient's arm.

The manufacturing process together with the process followed at the hospital or doctor's facility is set forth below. This combined process of molding cast system 10 as shown in part in FIGS. 1–4, is as follows:

a. setting out an inner layer 54 of resilient, water absorbing, fast drying material, such as sponge rubber or a foam plastic;

b. applying a middle layer of a plurality of laminated layers 56 of wet plaster of paris or other casting material to the face of the inner layer, c. applying an outer layer 60 of a flexible, soft, water absorbing fast drying material to the face of the middle layer 56 to form a layered wall comprising the inner, middle, and outer layers;

d. cutting out a form according to a pattern from the layered wall in accordance with the size of the molding cast 20 required;

e. stitching the edges of the formed layered wall and cross-stitching the formed layerd wall so as to form an integral wall member 22 having a pair of opposed elongated side edge portions 28 and 30 and a pair of opposed first and second end edge portions 32 and 34 respectively intersecting side edge portions 28 and 30;

f. attaching connectors 78, 80, 82 and 84 to the side edge portions;

g. attaching strap member 90 of sling 89 to wall member 22 at outer layer 60;

h. rolling up wall member 22 with connectors 78, 80, 82 and 84 and strap member 90 in preparation for shipment;

i. activating the intermediate molding cast layer subsequent to shipment prior to application to a patient wherein the intermediate molding cast is made soft and pliable by preferably placing the rigid intermediate molding cast in water or heat treating it;

j. after correcting the fracture to a normal position, applying the pliable molding cast to the arm of the patient wherein wall member 22 forms connecting, approximately cylindrical first and second chambers 24 and 26, respectively, first chamber 24 being generally horizontal and adapted to receive the under part and the side parts of the forearm of the patient between the hand and the elbow, second chamber 26 being generally vertical and adapted to receive the rear part and side parts of the upper arm of the patient extending from the elbow towards the shoulders to a position spaced from the elbow, with the first end edge portion 32 defining an approximately circular first opening 45 at the end of first chamber 24, and the second end edge portion 34 defining an approximately circular second opening 47 at the end of second chamber 26, the elongated side edge portions 28 and 30 defining an elongated aperture 48 opening to first and second chambers 24 and 26 along the top part of the forearm and the forward part of the upper arm; connectors 78, 80, 82 and 84 being adapted to adjustably and removably connect the side edge portions 28 and 30 across aperture 48 between the first and second circular openings 45 and 47, and sling 89 being adapted to adjustably support and position molding cast 22 so that first chamber 24 is kept in a generally horizontal position and second chamber 26 is maintained in a generally vertical position;

k. affixing connectors 78, 80, 82 and 84 across aperture 48 at the forearm and at the upper arm;

l. wrapping an "Ace" bandage (not shown) around the pliable molding cast to hold it in a desired cast position until the plaster of paris layer 56 in wall member 22 is rigid;

m. placing sling 89 around the neck of the patient to maintain the arm in the position desired; and n. removing the "Ace" bandage when the molding cast is rigid.

The embodiment of the invention particularly disclosed and described herein is presented merely as an example of the invention. Other embodiments, forms and modifications of the invention coming within the proper scope and spirit of the appended claims will, of course, readily suggest themselves to those skilled in the art.

What I claim is:

1. A molding cast system for fractures of the humerus and of the radius and ulna of a patient, comprising, in combination, a molding cast including a wall member defining connecting, approximately cylindrical first and second chambers, said wall member having a pair of opposed, spaced elongated side edge portions and a pair of first and second end edge portion intersecting said side edge portions, said first chamber being adapted to receive the under part and the side parts of the forearm of the patient between the hand area and the elbow area, said second chamber being adapted to receive the rear and side parts of the upper arm of the patient extending from the elbow area towards the shoulder area, said first end portion defining a first opening at the outer end of said first chamber and said second end edge portion defining a second first opening at the outer end of said second chamber, said elongated side edge portions defining an elongated aperture opening to said first and second chambers along the top part of said forearm and the forward part of said upper arm between said first and second openings;

said wall member including an inner layer of a flexible, porous material, a middle layer of a plurality of laminated layers of a casting material, and an outer layer of a flexible, soft, water absorbing and fast drying material;

means affixed to said side edge portions for adjustably and removably connecting said side edge portion across said aperture; and means for adjustably supporting and positioning said molding cast, wherein said first chamber is maintained in a generally horizontal position and said second chamber is maintained in a generally vertical position.

2. A molding cast system according to claim 1, wherein said plurality of laminated layers includes approximately twenty (20) laminated layers.

3. A molding cast system according to claim 2, wherein said means for connecting includes a plurality of connectors, each of said connectors comprising a first strap portion having fastening means thereon and being secured to one side of said wall member, and a second strap portion being secured to the other side of said wall member and having a ring member secured to the outer end thereof, said first strap portion extending across said aperture and through said ring member and being bent backwardly against itself and held in the bent position by said fastening means.

4. The molding cast system according to claim 3 wherein said fastening means are snag and hook fasteners.

5. A molding cast system according to claim 3 wherein said plurality of connectors includes four (4) connectors, one of said connectors being positioned at the upper arm area, two (2) of said connectors being positioned at the forearm area, and one (1) of said connectors being positioned at the hand area.

6. A molding cast system according to claim 1, wherein said supporting means comprises a strap member having opposed ends, a releasable fastener being connected to one of said ends, said strap being affixed to the underside of said molding cast and being adapted to extend around the neck of the patient, the other of said ends being adjustably connected to said releasable fastener.

7. A molding cast system according to claim 6 wherein said strap member passes through a pinching member positioned above said cast.

8. A molding cast system according to claim 1, wherein said inner layer is foam plastic.

9. A molding cast system according to claim 1, wherein said outer layer is a soft flannel.

10. A molding cast system according to claim 3, wherein said supporting means comprises a strap member having opposed ends, a releasable fastener being connected to one of said ends, said strap being affixed to the underside of said molding cast and being adapted to extend around the neck of the patient, the other of said ends being adjustably connected to said releasable fastener.

* * * * *

UNITED STATES PATENT OFFICE
CERTIFICATE OF CORRECTION

Patent No. 4,572,172                    Dated February 25, 1986

Inventor(s) L. Benton Williams

It is certified that error appears in the above-identified patent and that said Letters Patent are hereby corrected as shown below:

Column 8, Line 25, in Claim 1, for "portion", please read --portions--.

Column 8, Line 47, in Claim 1, for "portion", please read --portions--.

Signed and Sealed this

Twenty-seventh Day of May 1986

[SEAL]

Attest:

DONALD J. QUIGG

Attesting Officer    Commissioner of Patents and Trademarks